(12) United States Patent
Kusakabe et al.

(10) Patent No.: US 7,955,793 B2
(45) Date of Patent: Jun. 7, 2011

(54) CULTURED SILKWORM CELLS CAPABLE OF HIGHLY EFFICIENT BACULOVIRUS PRODUCTION AND PROTEIN PRODUCTION

(75) Inventors: Takahiro Kusakabe, Fukuoka (JP); Chisa Aoki, Fukuoka (JP); Osamu Ninagi, Fukuoka (JP); Jae Man Lee, Fukuoka (JP); Kazuhiro Iiyama, Fukuoka (JP); Naoya Kawakami, Fukuoka (JP)

(73) Assignee: Kyushu University, National University Corporation, Fukuoka-shi (JP)

( * ) Notice: Subject to any disclaimer, the term of this patent is extended or adjusted under 35 U.S.C. 154(b) by 0 days.

(21) Appl. No.: 12/226,689

(22) PCT Filed: Apr. 26, 2007

(86) PCT No.: PCT/JP2007/059028
§ 371 (c)(1),
(2), (4) Date: Jan. 28, 2009

(87) PCT Pub. No.: WO2007/125982
PCT Pub. Date: Nov. 8, 2007

(65) Prior Publication Data
US 2009/0305385 A1 Dec. 10, 2009

(30) Foreign Application Priority Data
Apr. 27, 2006 (JP) ................................. 2006-122943

(51) Int. Cl.
*C12Q 1/70* (2006.01)
(52) U.S. Cl. .......................................................... 435/5
(58) Field of Classification Search ........................ None
See application file for complete search history.

(56) References Cited

OTHER PUBLICATIONS

Guo et al (Archives of Virology, 2005 [Available on line Sep. 21, 2004], vol. 150, pp. 93-105).*

Motohashi et al (Biochemical and Biophysical Research communications, 2005 [Available online Nov. 24, 2004] vol. 326, pp. 564-569).*
Lee et al, Journal of Insect Biotechnology and Serocology, 2007, vol. 76, pp. 101-105.*
Imanishi, S. et al, "Characteristics of cell lines established from embryonic tissues of several races of the silkworm, Bombyx mori, cultured in vitro," J. Seric., Sci. Jpn., 1988, vol. 57, No. 3, pp. 184-188.
Imanishi, S. et al, "Novel Bombyx mori cell lines cultivable at 37°C," Appl. Entomol. Zool., May 25, 1999, vol. 34, No. 2, pp. 259-266.
Imanishi, S. et al, "Suspension-type Cloned Cell Lines from Embryo Tissues of Bombyx mori," JARQ, 1992, vol. 26, No. 3, pp. 196-202.
Inoue, H. et al, "A Bombyx mori Cell Line Susceptible to a Nuclear Polyhedrosis Virus," J. Seric. Sci. Jpn., 1984, vol. 53, No. 2, pp. 108-113.
Inoue, H. et al, "Establishment and characterization of substrate-depending cell lines of Bombyx mori," Bull. Natl. Inst. Seric. Entomol. Sci., 1990, vol. 1, pp. 13-25.
JPO International Search Report, Appl. No. PCT/JP2007/059028, Jul. 17, 2007, pp. 1-5.
Suzuki, Y. et al, "Tissue-specific transcription enhancement of the fibroin gene characterized by cell-free systems," Proc. Natl. Acad. Sci., Dec. 1986, vol. 83, No. 24, pp. 9522-9526.

* cited by examiner

*Primary Examiner* — Ali R. Salimi
(74) *Attorney, Agent, or Firm* — Birch, Stewart, Kolasch & Birch, LLP

(57) ABSTRACT

Known cell lines derived from silkworm exhibit low propagation efficiency of BmNPV. Accordingly, systems using known culture cell lines derived from silkworms take a long time to establish recombinant viruses, and are not suitable for preparation of virus solutions with high titers. The present invention provides a cell line Bme21 (FERM P-20852) that is derived from a silkworm embryo and is highly susceptible to BmNPV or its variant having the same biological characteristics. The present invention also provides a method of producing a recombinant virus, a method of producing a recombinant protein, a method of increasing efficiency of recombinant virus production, and a method of increasing efficiency of recombinant protein production, using the cell line Bme21 or its variant.

8 Claims, 2 Drawing Sheets

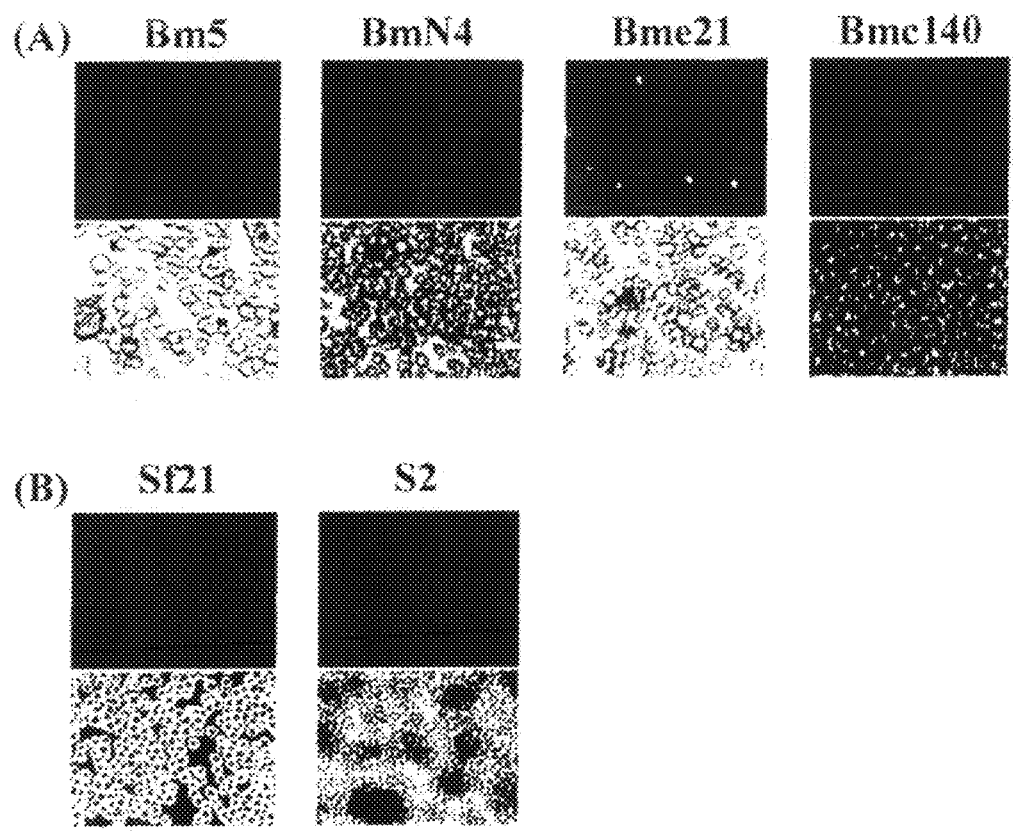

US 7,955,793 B2

CULTURED SILKWORM CELLS CAPABLE OF HIGHLY EFFICIENT BACULOVIRUS PRODUCTION AND PROTEIN PRODUCTION

TECHNICAL FIELD

The present invention relates to insect-derived culture cells. The novel silkworm-embryo-derived cell lines obtained by the present invention are useful particularly in production and assay of recombinant baculovirus and in production of a recombinant protein.

BACKGROUND ART

Recombinant protein expression systems using insects are emphasized because they can produce modified proteins similar to those produced in mammalian cells in relatively large amounts. In systems using insects, it has been investigated to use nucleopolyhedrovirus (NPV), in particular, BmNPV or AcNPV as a vector, in which BmNPV can infect *Bombyx mori*, and AcNPV can infect *Autographa californica* (one of Plusiinae) and *Spodoptera litura*, but usually does not infect silkworm. From the viewpoint of host cells, the systems using insects are roughly classified into systems using culture cells and systems using insect individuals. In recent years, AcNPV-*Spodoptera litura* culture cell lines have been widely used, while BmNPV-silkworm individual systems are now in the process being used.

Systems using insect culture cell lines have advantages over systems using insect individuals, that is, they can treat a large number of specimens without human intensive.

Silkworm-derived culture cells hitherto reported are, for example, those derived from embryonic tissue slices of silkworm strain "Kuroko" (Non-Patent documents 1 and 2), those derived from embryonic tissue of silkworm strain "J125" (Non-Patent documents 3 and 4), those derived from embryonic tissue of silkworm strain "C129" (Non-Patent document 3), those derived from an embryonic head section of silkworm strain "Gominhaku" (Non-Patent document 5), and those derived from embryonic tissue slices of silkworm strains "Murasakiko", "Black moth", "Daizo", and "Sepialumazine" (Non-Patent document 6).

Non-Patent document 1: Inoue, H. and Mitsuhashi, J., A *Bombyx mori* cell line susceptible to a nuclear polyhedrosis virus; J. Seric. Sci. Jpn. 53, 108-113 (1984).
Non-Patent document 2: Inoue, H., Taniai, M., and Kobayashi, J., Kaiko no fuchaku-sei baiyosaibo-kei no juritsu to sono tokusei (Establishment and characterization of adhesive cell lines of silkworm); Sanshi-Konchu Ken-Ho (Bull. Natl. Inst. Seric. Entomol. Sci.) 1, 13-25 (1990).
Non-Patent document 3: J. Seric, Sci. Jpn. 57(3), 184-188 (1988).
Non-Patent document 4: JARQ 26, 196-202 (1992).
Non-Patent document 5: Imanishi, S., Kaiko taieki ni hannou shie kaitai henka wo okosu baiyousaibo-kei no sakusyutsu (Establishment of culture cell line producing morphology change by silkworm body fluid); Nichi-San Kanto Shibu Koyo (Abstracts Jpn. Seric. Kanto Dev.) 50, 40 (1999).
Non-Patent document 6: Imanishi, S., Cho, E. S., and Tomita, S., Novel *Bombyx mori* cell lines cultivable at 37° C.; Appl. Entomol. Zool. 34, 259-266 (1999).

DISCLOSURE OF THE INVENTION

Problems to be Solved by the Invention

However, most of the practical silkworm strains are virus insusceptible. This is resulted from screening of strains insusceptibility to viruses as a useful morphology, because silkworms not resistance to viruses are unsuitable for producing yarn. Accordingly, cell lines established from such strains exhibit low efficiency of propagation of BmNPV. Therefore, systems using known culture cells derived from silkworms require long hours for production of recombinant viruses and cannot prepare virus solutions with high titers.

Means for Solving the Problems

The present inventors have analyzed insects using an abundant stock of resources for their reproduction, development, meiosis, and replication, and repair, recombination, and expression mechanisms of genes, by molecular genetic, cell biological, morphologic, and molecular biological techniques. In addition, the inventors have investigated production of useful materials using a baculovirus expression system in order to develop and utilize novel insect functions and have established culture cell line Bme21 from an embryo derived from a specific silkworm strain. Furthermore, the inventors have found that this culture cell line has virus particle productivity that is at least 100 times higher than those of known culture cell lines derived from silkworm, and the present invention has been accomplished.

The present invention provides a cell line Bme21 (FERM P-20852) that is derived from a silkworm embryo and is highly susceptible to BmNPV, or its variant having the same biological characteristics; and a cell line that is obtained from a primary culture of an embryo of silkworm strain e21 and is highly susceptible to BmNPV.

Throughout the description, the term "silkworm" indicates a *Bombyx mori* individual, except otherwise stated, and includes not only a larva individual but also egg, pupa, cocoon, and imago individuals.

In the description, the term "strain" of the silkworm means a family of silkworms that can be distinguished from other families of strains by the total or partial characteristics (morphologies of egg, larva, pupa, cocoon, and imago, and genotype) and genesis and that can be propagated while retaining all the characteristics. The "strain" may be expressed as "variety".

In the description, the term "susceptibility" means ability to be infected with a virus and propagate the virus, except otherwise stated. Susceptibility to BmNPV can be determined, for example, as shown in Examples of this description, by establishing a recombinant virus containing a gene encoding a protein by which propagation of BmNPV can be readily evaluated (for example, luciferase recombinant BmNPV or GFP recombinant BmNPV), infecting target cells with the recombinant virus and evaluating the amount of the protein at a suitable stage or infecting target cells with the recombinant virus and evaluating the titer of the virus in a culture supernatant by plaque assay. Sf9 cells (culture cell derived from the ovary of *Spodoptera frugiperda*) and S2 cells (cell derived from an embryo of *Drosophila melanogaster*) are not infected with BmNPV or cannot propagate BmNPV and are therefore susceptible to BmNPV.

The cell of the present invention has high susceptibility to BmNPV. The term "high susceptibility" means that BmNPV propagates at least 5 times, preferably at least 10 times, and more preferably at least 100 times those in conventional BmNPV-susceptible cells (e.g., BmN4 (refer to Table 1 and Examples below), Bm5 (refer to Table 1 and Examples below), or BM-N(RIKEN)); the luciferase activity can be higher than $10^3$ RLU/μg and preferably higher than $10^4$ RLU/μg where luciferase is used as an indicator under the conditions shown in Examples of this description; the infection can be recognized in at least 50%, preferably at least 75%, and more preferably at least 90% of specimen cells where GFP is used as an indicator under the conditions shown in Examples of this description; or the infection can be detected in at least 50%, preferably at least 75%, and more preferably at least 90% of specimen cells where plaque formation is used as an indicator under the conditions shown in Examples of this description.

"Cell line Bme21" according to the present invention is established from silkworm strain e21 through primary culture and can be semipermanently subcultured. The present inventors found that silkworm strain 21 tends to be readily infected with baculovirus. Various silkworm strains containing e21 are available from Institute of Genetic Resources, Kyushu University (Graduate School of Faculty of Agriculture, Kyushu University: 6-10-1 Hakozaki, Higashi-ku, Fukuoka-city, Fukuoka 812-8581 Japan; (Tel) 092-621-4991, (Fax) 092-624-1011, HYPERLINK: "mailto:fujii@agr.kyushu-u.ac.jp"), which is a core institution of National Bio Resource Project (NBRP) (refer to http://www.nbrp.jp/report/report-Project.jsp;
jsessionid=BE73451C6E54680014762FD194C0F721?project=silkworm).

Characteristics of Bme21:
Species: silkworm, *Bombyx mori* e21 strain
Tissue: egg
Morphology: adhesive and mostly spherical (refer to FIG. 1)
Culture medium: IPL-41 medium+10% FBS
Incubation temperature: 27° C.,
$CO_2$ level: 0%
Doubling time: 60 hours
Method of subculture: dilution
Subculture frequency: once every four or five days
Lifespan: infinite
Others: highly susceptible to BmNPV and insusceptible to AcNPV Characteristics of Bme21 in comparison to those of other insect culture cells are shown in the following Table.

The scope of the present invention includes a cell line e21 and a variant thereof having the same biological characteristics as those of the cell line e21.

Cell line Bme21 was deposited on Mar. 24, 2006 under Deposition No. FERM AP-20852 (Accession No. FERM AP-20852) at International Patent Organism Depositary, National Institute of Advanced Industrial Science and Technology (Central 6, 1-1-1, Higashi, Tsukuba-shi, Ibaraki 305-8556 Japan), and also can be obtained from an embryo of silkworm stain e21.

The cell line can be established from a silkworm embryo as follows:

1. Silkworm eggs at any stage from head pigmentation to body pigmentation are removed from a card and are sterilized with 1% sodium hypochlorite (NaOCl);
2. Ten of the sterilized eggs are fixed with surgical Aron Alpha on a plastic plate (about 1 cm by 2 cm);
3. The eggs are cut with a sharp knife to extract the embryos (larvae) at any stage from head pigmentation to body pigmentation;
4. The larvae are immersed in 1% sodium hypochlorite for about 10 seconds for sterilizing the surfaces, washed with sterile distilled water twice, and placed into a 35 cm plastic petri dish containing 2 mL of an IPL-41 medium containing 20% FBS;
5. Each of the larvae in the petri dish is cut into five to ten pieces with ophthalmic scissors, and the medium containing the larva pieces is transferred into a 50 mL plastic culture flask, followed by supplement of 1 mL of a flesh medium; and
6. Incubated is carried out at 26° C.

The inventors' trials for establishment of culture cell lines using various silkworm strains showed that the cells was able to be cultured for about 60 days after the start of the primary cultures, but then suddenly died, in many cases. Therefore, cells that can be subcultured for at least 90 days can be recognized to be established as a cell line.

TABLE 1

Morphologic characteristics of culture cells and susceptibility to BmNPV

| Cell lines | Origin | Morphological characteristics | Doubling time | BmNPV-susceptibility (see Examples) | Others |
|---|---|---|---|---|---|
| BmN4 | *Bombyx mori*, ovary | adherent | 60 h | + | |
| Bm5 | *Bombyx mori* | adherent | 70 h | + | |
| Bme21 | *Bombyx mori*, embryo | adherent | 60 h | +++ | |
| Bmc140 | *Bombyx mori*, ovary | floating | 80 h | + | Low efficiency of gene transduction due to floating |
| Sf9 | *Spodoptera frugiperda*, ovary | adherent | 50 h | − | |
| S2 | *Drosophila melanogaster*, embryo | adherent | 4 h | − | |

BmN4: cell line cloned from silkworm-origin culture cell line BmN (unpublished) by Dr. Maeda, Susumu, and obtained from Dr. Hashimoto, Yoshifumi, former Faculty of Fiber, Kyoto Institute of Technology, 1992.
Bm5: obtained from Dr. Sato, Takeshi, former Fruit Experimental Station, in 1990.
Bmc140: derived from the pupal ovary of a silkworm strain "C140", established by Dr. Sato, Takeshi, former Fruit Experimental Station and obtained from Dr. Sato, Takeshi (published as BmX, the former name, by poster presentation in SIP2000 held in Mexico).
Sf9: purchased from Invitrogen.
S2: purchased from RIKEN cell bank.

Basically, the same culture medium can be used throughout the primary culture. The culture medium can be changed as appropriate according to the growth of the cells for the initial 60 days and then be changed once every about three to four days. It is better to add about 20% serum to the culture medium at first, but the amount of the serum can be reduced to about 10% after the growth of the cells becomes steady. In some cases, the primary culture can be carried out in a medium other than the above-mentioned medium, for example, in Grace's medium, IPL-41 medium, Schneider's *Drosophila* medium, Sf900II, TC-100 medium, Sf-9 cell medium, Sf-21 cell medium, Express Five medium, or EX-400 medium.

Processes necessary for culturing, for example, subculture of cell line e21 and its variants having the same biological characteristics of cell line e21 of the present invention and freezing of the cell lines for storage, can be carried out by those in the art as appropriate according to the usual cases of insect cells.

The present invention also provides a method of producing a recombinant virus, a method of producing a recombinant protein, a method of increasing efficiency of a recombinant virus production, and a method of increasing efficiency of a recombinant protein production, using a cell line Bme21 or its variant.

The use of the cell line Bme21 of the present invention enables a recombinant protein to be produced at a high efficiency that is at least 100 times those of systems using known silkworm culture cells. Accordingly, the present invention can be applied to the production of a protein that can be produced in a significantly small amount in any conventional system using known silkworm culture cells and that could not accept a baculovirus-silkworm cell system as an alternative in actual production. In addition, the use of the cell line Bme21 derived from silkworm of the present invention may allow a protein having a modification that is different from those in known AcNPV-insect culture cell lines to be produced. In general, in insect culture cell lines, a larger number of specimens can be treated at the same time compared to cases using insect individuals. In addition, the present invention is advantageous in that the culture of insect cell lines does not require specific facilities and operations that are necessary for the culture of insect individuals and thus can be simply carried out using common instruments and facilities for culturing mammalian cells. Furthermore, the present invention allows baculovirus-silkworm culture cell lines to be applied to produce various proteins. In particular, the present invention is suitable for small-scale to medium-scale production of recombinant proteins, for example, production of several milligrams of a protein in several liters of culturing medium.

The present invention can also be used for assay of recombinant viruses. Since recombinant viruses are produced using live cells, unexpected recombination may occur. In particular, when recombination is carried out using a gene encoding a protein having a physiological activity, an expected recombinant may be hardly obtained. However, the use of e21 cells having high propagation efficiency and high protein productivity of the present invention can assay a recombinant virus expressing a target protein in a short period of time by simplified procedures, for example, by only electrophoresis and pigment dyeing. Accordingly, the present invention is useful to the assay of recombinant viruses and preliminary experiments of protein production. The present invention is particularly suitable for high-throughput recombinant virus production capable of treating a large number of specimens at the same time.

BRIEF DESCRIPTION OF THE DRAWINGS

FIG. 3 is photographs showing propagation of recombinant BmNPV viruses (expressing GFP), wherein the amount of the GFP expressed in Bme21 cells is the highest, compared to other culture cells derived from silkworm, and most of the cells express GFP.

EXAMPLES

Figure 1:
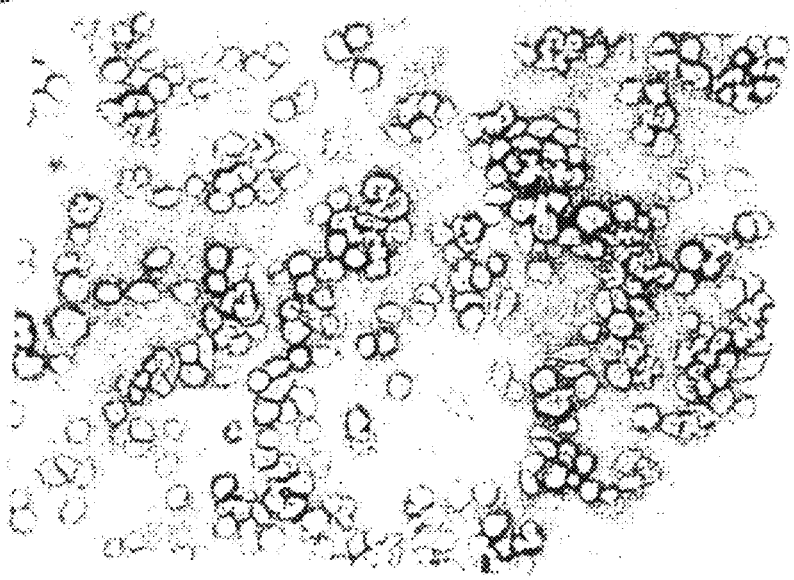
FIG. 1 is a micrograph of a cell line Bme21 derived from a silkworm embryo of the present invention, the Bme21 being adhesive and mostly spherical.

1. Material and Method 1.1 Primary Culture of Silkworm Mature Embryo

Eggs of silkworm strain e21 (possessed by Graduate School of Faculty of Agriculture, Kyushu University) at any stage from head pigmentation to body pigmentation were left at 25° C. for about 9 days, then were removed from a card, and were sterilized with 1% sodium hypochlorite (NaOCl). Ten of the sterilized eggs were fixed on about a plastic plate (1 cm and 2 cm) with surgical Aron Alpha. The eggs were cut with a sharp knife to extract the embryos (larvae) at any stage from head pigmentation to body pigmentation. The larvae were immersed in 1% sodium hypochlorite for about 10 seconds for sterilizing the surfaces, washed with sterile distilled water twice, and placed into a 35-cm plastic petri dish containing 2 mL of an IPL-41 medium containing 20% FBS (Gibco BRL). Each of the larvae in the petri dish was cut into five to ten pieces with ophthalmic scissors, and the medium containing the larva pieces was transferred into a 50 mL plastic culture flask (tissue culture flask 50 mL, 25 cm$^2$, manufactured by Greiner), followed by supplement of 1 mL of a flesh medium. Then, incubation was carried out at 26° C. The resulting cells were used as a cell line Bme21 in the following experiments.

1.2 Cell Culture and Preparation of Recombinant BmNPV

Silkworm-origin culture cell lines BmN4 (cell line cloned from silkworm-origin culture cell line BmN by Dr. Maeda, Susumu, and obtained from Dr. Hashimoto, Yoshifumi, former Faculty of Fiber, Kyoto Institute of Technology), Bm5 (obtained from Dr. Sato, Takeshi, former Fruit Experimental Station), Bmc140 (derived from the pupal ovary of a silkworm strain "C140", obtained by Dr. Sato, Takeshi, former Fruit Experimental Station), and Bme21, and *Mamestra*-origin culture cell line Sf9 (purchased from Invitrogen) were each cultured in an IPL-41 medium (Gibco BRL) containing 10% FBS at 23° C. for testing. A *drosophila*-origin culture cell line S2 (purchased from RIKEN cell bank) was cultured in a Schneider's *Drosophila* medium (Gibco BRL) containing 10% FBS at 27° C. for testing. All processes were carried out aseptically in a clean bench.

The old culture medium was removed from each flask containing the culture cells, and 8 mL of a flesh culture medium was added to the flask. The cells were dispersed by pipetting to give a single cell state. The dispersed cells (1 mL) were transferred to another flask containing 7 mL of a culture medium to give a total amount of 8 mL. The flask was put in an incubator for incubation.

A bacmid DNA was constructed using a BmNPV Bac-to-Bac system. First, a cDNA encoding firefly luciferase or GFP was inserted in a multicloning site of pFastBac (Invitrogen) to give pFastBac/Luc or pFastBac/GFP, respectively. The pFastBac includes an attTn7 recognition sequence for transposition to a bacmid DNA and a gentamicin resistance gene as a selective marker. The luciferase or GFP expression cassette on the pFastBac/Luc or pFastBac/GFP was introduced into the BmNPV genome using a BmNPV Bac-to-Bac Baculovirus Expression System (refer to Motohashi T, Shimojima, T., Fukagawa, T., Maenaka, K., and Park, E. Y., Efficient large-scale protein production of larvae and pupae of silkworm by Bombyx mori nuclear polyhedrosis virus bacmid system. Biochem. Biophys. Res. Commun., 326, 564-569 (2005)). First, the pFastBac/Luc or pFastBac/GFP was transformed into BmDH10Bac, incubated at 37° C. for 4 hours, and then inoculated on an LB plate containing kanamycin, gentamicin, tetracycline, Bluo-gal, and IPTG. After still leaving to stand at 37° C. for one day, white colonies were collected with a platinum loop and cultured in 1.5 mL of an LB medium. Subsequently, bacmid DNA was extracted. The extraction of the bacmid DNA was preformed by an alkali-SDS method.

The culture solution (1.5 mL) was centrifuged at 14000 g for one minute to collect the cells, which were then suspended and stirred completely in 300 mL of 10 mM EDTA, 15 mM Tris-HCl (pH 8.0), and 100 mg/mL RNase A. Then, 300 mL of 0.2 N NaOH and 1% SDS were added. After gentle mixing, the mixture was left for standing at room temperature for five minutes. After 300 mL of 3M potassium acetate (pH 5.5) was further added and mixed well. The mixture was left for standing in ice for five minutes and then centrifuged at 14000 rpm for 10 minutes at 4° C. The collected supernatant was subjected to isopropanol precipitation. The precipitate was dissolved in 40 mL of a solution (TE) containing 1 M Tris (pH 8.0) and 0.5 M EDTA (pH 8.0), and used as a bacmid sample.

The Bm5 cells were used as host cells for BmNPV propagation. Transfection into the Bm5 cells was performed as follows: On the day before transfection, the cells were dispersed and seeded in a 24-well plate at $1\times10^5$ cells/well, followed by culturing at 23° C. for one day. Bacmid DNA (0.5 mg) was diluted with HBS into 10 mL per well and used as solution A. Separately, 4 mL of CellFectin (GIBCO BRL) was diluted with 16 mL of HBS and incubated on ice for 45 minutes. During a waiting period of 45 minutes, the cells were washed with SFM (GIBCO BRL) once. In order to form a conjugate of cation lipid and DNA, incubation was continued in ice for additional 15 minutes. After addition of 170 mL of SFM to the mixture solution, the medium in each well was removed and the mixture solution was added to the cells. After culturing at 23° C. for 8 hours, the transfection mixture solution was removed and replaced by 1 mL of 10% FBS-containing Grace's Insect Medium (Gibco BRL), followed by further culturing. After culturing at 27° C. for three days, the culture solution was collected and sterilized by filtration to give a baculovirus-containing solution (P1 virus solution). With this P1 virus solution (10 mL), $5\times10^5$ host cells were infected. After three days, the virus solution was collected (P2 virus solution). The P2 virus solution was also amplified in the same manner to give a P3 virus solution, which was used for the inoculation experiment.

1.3 Propagation of Virus Using Luciferase as an Indicator

The cells ($1\times10^5$ cells/per well) were inoculated with the P3 virus solution that expresses luciferase at an m.o.i. of 0.5. The inoculated cells were collected at 12, 24, 72, or 120 hours after the inoculation and were transferred to a 1.5 mL Eppendorf tube. The tube was centrifuged at 2000 rpm for one minute at 4° C. to collect the cells. The culture solution was removed, and the cells were washed with PBS twice, followed by addition of a cell lysis solution (100 μL). The cells were left at room temperature for 15 minutes or longer and then centrifuged at 10000 rpm for 30 seconds at 4° C. A luminescence substrate solution (100 μL) was added to 80 μL of the resulting cell extract for measuring the luminescence intensity of the luciferase with a luminometer. The remaining 20 μL of the cell extract was subjected to quantitative determination of protein for correction of the luciferase activity.

1.4 Propagation of Virus Using GFP as an Indicator

The cells ($1\times10^5$ cells/per well) were inoculated with the P3 virus solution that expresses GFP at an m.o.i. of 0.5. The inoculated cells were collected 48 hours after the inoculation and were observed with a fluorescence microscope.

1.5 Propagation of Virus Using Plaque Formation as an Indicator

The cells ($1\times10^5$ cells/per well) were inoculated with the P3 virus solution that expresses luciferase at an m.o.i. of 0.5. The culture supernatants were collected at 12, 24, 72, or 120 hours after the inoculation and were each transferred to a 1.5-mL Eppendorf tube. The tube was centrifuged at 2000 rpm for one minute at 4° C. to remove the precipitate. Each culture supernatant was subjected to plaque assay measuring the virus titer. Bm5 cells were seeded in a 6-well plate at $1\times10^5$ cells/per well, followed by incubation at 27° C. for one hour. The medium of each well was removed, and 1 mL of each culture supernatant of virus dilution series was added to the respective wells. After incubation at 27° C. for 1 hour, each virus dilution solution was removed. Furthermore, 2 mL of a 1% low-melt agarose solution was added to each well, followed by incubation at 27° C. for 4 to 6 days. Finally, 1 mL of 1% low-melt agarose solution containing NR (neutral red) was layered, followed by incubation at 27° C. overnight. The virus titer (pfu/mL) was calculated based on the number of plaques formed. This process was repeated twice, and the average was used as the virus titer value.

2. Results 2.1 Propagation of Virus Using Luciferase as an Indicator

Figure 2:
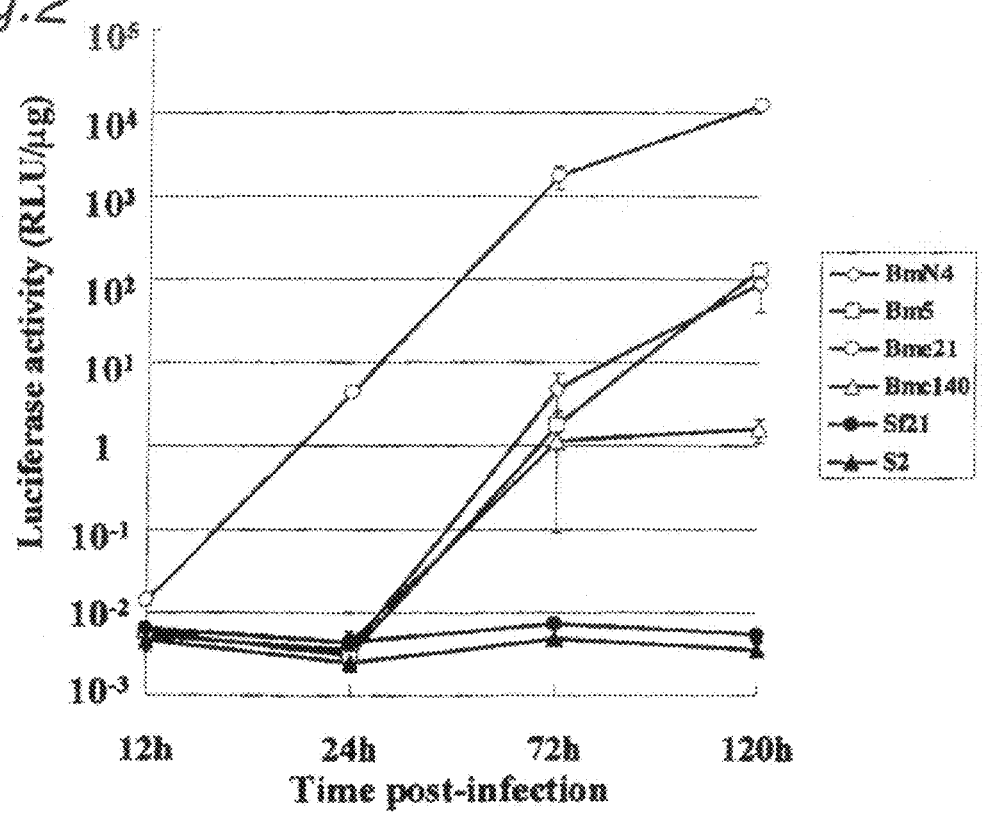
FIG. 2 is a graph showing propagation of a recombinant BmNPV viruses (expressing luciferase), wherein the luciferase activity curve of Bme21 cells rises at an early stage compared to other culture cells derived from silkworm, and the activity reaches a level at least 100 times of those of Bm5 and BmN4 after 100 hours.

The luciferase activity curve of Bme21 cells rose at an early stage compared to other culture cells derived from silkworm, and the activity reached a level at least 100 times those of Bm5 and BmN4 after 120 hours (FIG. 2).

2.2 Propagation of Virus Using GFP as an Indicator

The amount of the GFP expressed in Bme21 cells was the highest, compared to those in other culture cells derived from silkworm, and most of the cells expressed the GFP (FIG. 3). The results demonstrate that Bme21 cells are most suitable for propagation of recombinant BmNPV virus.

2.3 Propagation of Virus Using Plaque Formation as an Indicator

Bme21 cells showed a higher virus titer (pfu/mL), compared to those in other culture cells derived from silkworm, and the titer reached a level almost 1000 times those of Bm5 and BmN4 after 120 hours (Table below).

[Table 2]

TABLE 2

Propagation of virus using plaque formation as an indicator

| | Time (h) post-infection | | | |
|---|---|---|---|---|
| Cell lines | 12 | 24 | 72 | 120 |
| BmN4 | $1.7 \times 10^2$ | $1.6 \times 10^2$ | $1.9 \times 10^3$ | $4.0 \times 10^4$ |
| Bm5 | $1.5 \times 10^2$ | $1.2 \times 10^2$ | $5.0 \times 10^2$ | $2.5 \times 10^4$ |
| Bme21 | $1.3 \times 10^2$ | $2.1 \times 10^3$ | $9.0 \times 10^6$ | $3.2 \times 10^7$ |
| Bmc140 | $1.1 \times 10^2$ | $1.0 \times 10^2$ | $8.8 \times 10^2$ | $9.4 \times 10^2$ |

TABLE 2-continued

Propagation of virus using plaque formation as an indicator

| Cell lines | Time (h) post-infection | | | |
|---|---|---|---|---|
| | 12 | 24 | 72 | 120 |
| Sf21 | $1.4 \times 10^2$ | $1.9 \times 10^2$ | $1.6 \times 10^2$ | $2.1 \times 10^2$ |
| S2 | $1.5 \times 10^2$ | $0.6 \times 10^2$ | $0.8 \times 10^2$ | $1.0 \times 10^2$ |

The invention claimed is:

1. A method of producing a recombinant baculovirus comprising:
   growing cells from a cell line obtained from a silkworm embryo and deposited as Accession No FERM P-20852 (Bme21 cell line) in a culture;
   inoculating the cells with a recombinant baculovirus; and
   harvesting the recombinant baculovirus from the cell culture.

2. A method of producing a recombinant protein comprising:
   growing cells from a cell line obtained from a silkworm embryo and deposited as Accession No FERM P-20852 (Bme21 cell line) in a culture;
   inoculating the cells with a recombinant baculovirus;
   expressing a recombinant protein; and
   harvesting the recombinant protein from the cell culture.

3. A method of increasing an amount of recombinant viral particles produced in cells, which method comprises:
   growing cells from a cell line obtained from a silkworm embryo and deposited as Accession No FERM P-20852 (Bme21 cell line) in a culture;
   inoculating the cells with a recombinant baculovirus; and
   collecting the recombinant viral particles from the cell culture,
   wherein the amount of recombinant viral particles produced in the silkworm cells from the Bme21 cell line is greater than the amount of recombinant viral particles produced in silkworm cells, other than the silkworm cells from the Bme2l cell line, which are inoculated with the recombinant baculovirus.

4. A method of increasing an amount of recombinant protein produced from cells, which method comprises:
   growing cells from a cell line obtained from a silkworm embryo and deposited as Accession No FERM P-20852 (Bme21 cell line) in a culture;
   inoculating the cells with a recombinant baculovirus;
   expressing a recombinant protein; and
   harvesting the recombinant protein from the cell culture,
   wherein the amount of recombinant protein produced by the silkworm cells from the Bme21 cell line is greater than the amount of recombinant protein produced from silkworm cells, other than the silkworm cells from the Bme2l cell line, which are inoculated with the recombinant baculovirus.

5. The method according to claim 1, wherein the baculovirus is a *Bombyx mori* nucleopolyhedrovirus.

6. The method according to claim 2, wherein the baculovirus is a *Bombyx mori* nucleopolyhedrovirus.

7. The method according to claim 3, wherein the baculovirus is a *Bombyx mori* nucleopolyhedrovirus.

8. The method according to claim 4, wherein the baculovirus is a *Bombyx mori* nucleopolyhedrovirus.

* * * * *